US007778848B1

(12) United States Patent
Reeves

(10) Patent No.: US 7,778,848 B1
(45) Date of Patent: Aug. 17, 2010

(54) ELECTRONIC SYSTEM FOR RETRIEVING, DISPLAYING, AND TRANSMITTING STORED MEDICAL RECORDS FROM BODILY WORN OR CARRIED STORAGE DEVICES

(75) Inventor: William Francis Reeves, North Branford, CT (US)

(73) Assignee: Quantum Innovations, LLC, North Brunford, CT (US)

( * ) Notice: Subject to any disclaimer, the term of this patent is extended or adjusted under 35 U.S.C. 154(b) by 891 days.

(21) Appl. No.: 09/583,336

(22) Filed: May 31, 2000

(51) Int. Cl.
*G06F 19/00* (2006.01)
*G06Q 50/00* (2006.01)

(52) U.S. Cl. .............................. 705/3; 705/2
(58) Field of Classification Search ................. 705/2–4; 600/300
See application file for complete search history.

(56) References Cited

U.S. PATENT DOCUMENTS

| | | | | |
|---|---|---|---|---|
| 4,941,201 A | * | 7/1990 | Davis ......................... | 455/41.2 |
| 5,337,290 A | * | 8/1994 | Ventimiglia et al. ............ | 368/10 |
| 5,499,626 A | * | 3/1996 | Willham et al. .............. | 600/300 |
| 5,615,268 A | * | 3/1997 | Bisbee et al. ................ | 713/176 |
| 5,678,562 A | * | 10/1997 | Sellers ........................ | 600/523 |
| 5,693,076 A | * | 12/1997 | Kaemmerer .................. | 607/59 |
| 5,995,077 A | * | 11/1999 | Wilcox et al. ................ | 715/841 |
| 6,021,393 A | * | 2/2000 | Honda et al. .................... | 705/3 |
| 6,188,407 B1 | * | 2/2001 | Smith et al. .................. | 345/841 |
| 6,401,206 B1 | * | 6/2002 | Khan et al. ................... | 713/176 |
| 6,681,003 B2 | * | 1/2004 | Linder et al. ........... | 379/106.02 |
| 6,747,561 B1 | * | 6/2004 | Reeves ..................... | 340/573.1 |

FOREIGN PATENT DOCUMENTS

| | | | |
|---|---|---|---|
| WO | WO 97/22297 A1 | * | 6/1997 |
| WO | WO9722297 A1 | * | 6/1997 ..................... 5/117 |

OTHER PUBLICATIONS

Castelluccio, Michael, "Wearable Computers", Management Accounting, Apr. 1997, vol. 78, No. 10, pp. 60-62.*
Warren, Designing smart health care technology into the home of the future, in Proc. 1st Joint BMES/EMBS Conf., Atlanta, GA, 1999, p. 677.*

* cited by examiner

*Primary Examiner*—Luke Gilligan
*Assistant Examiner*—Tran Nguyen

(57) ABSTRACT

A seamless and compatible system comprised of various hardware and software components for storing and carrying digital medical records on bodily worn devices, accessing said medical records from bodily worn devices via wireless interface wands, displaying said medical records on portable hand held devices and screens, transmitting said medical records to either base unit computers or patient monitoring modules in emergency rooms, Also disclosed are unique methods for organizing and prioritizing said medical records via a unique weighted average risk factoring based on pre-existing conditions, access to medical records and prognosis during treatment. Also disclosed is a unique means of interfacing the system to the Internet to access said medical records from remote locations and for convenient updating of said records via remote locations.

20 Claims, 11 Drawing Sheets

FIG. 4

Figure 1:
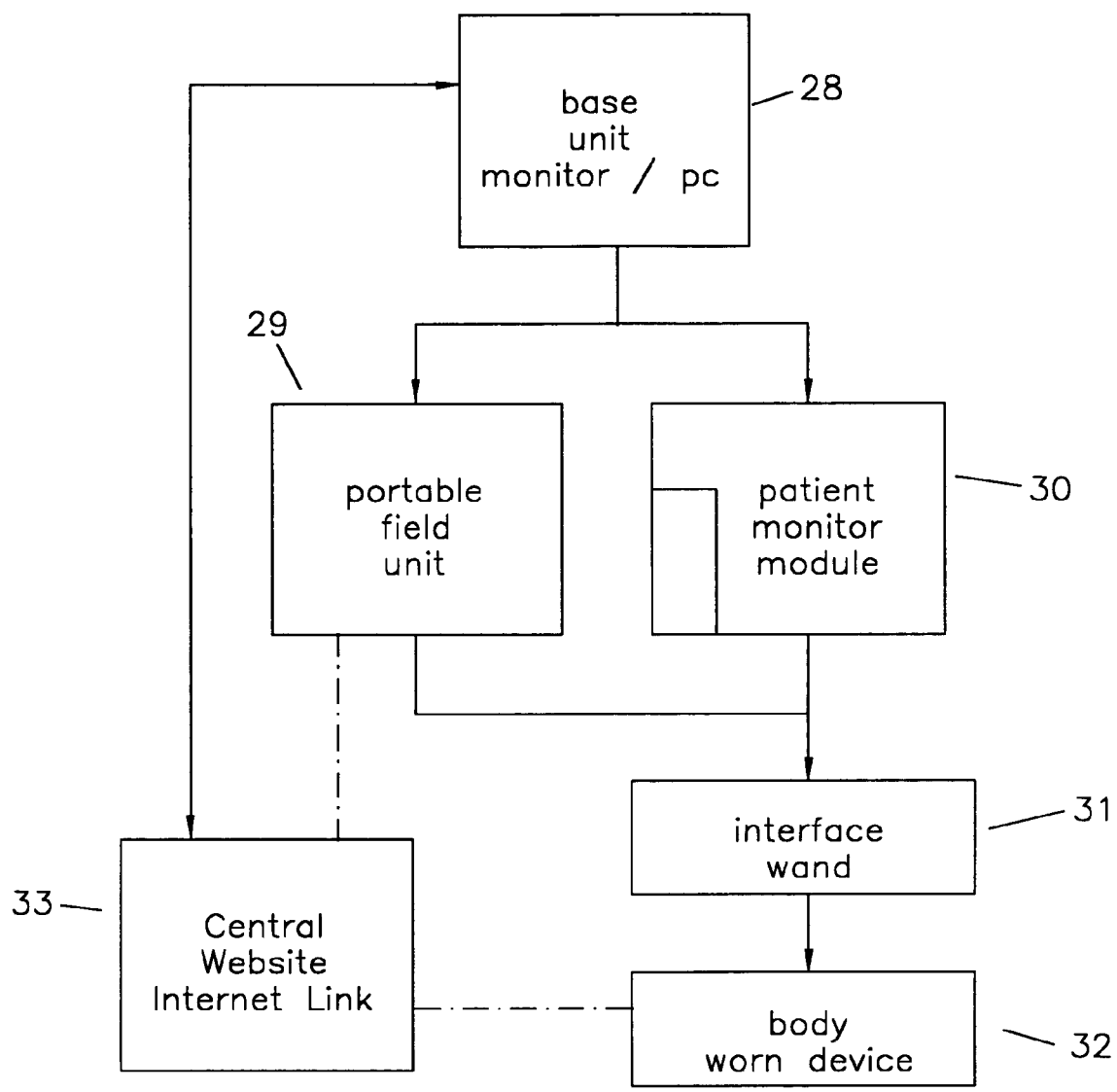

| PHOTO I.D. | FINGER PRINT | IRIS PRINT | DENTAL RECONDS | SAMPLE ECG ULTRASOUND |
|---|---|---|---|---|
| EMERGENCY MECIDAL RECORDS<br>BLOOD TYPE<br>DRUG REACTIONS<br>PRE-EXISTING CONDITIONS ||||||
| EMERGENCY TREATMENT INSTRUCTIONS:<br>PHYSICIAN<br>PRE-EXISTING CONDITIONS ||||||
| ORGAN DONOR INSTRUCTIONS: ||||||
| LIVING WILL INSTRUCTIONS: ||||||

16

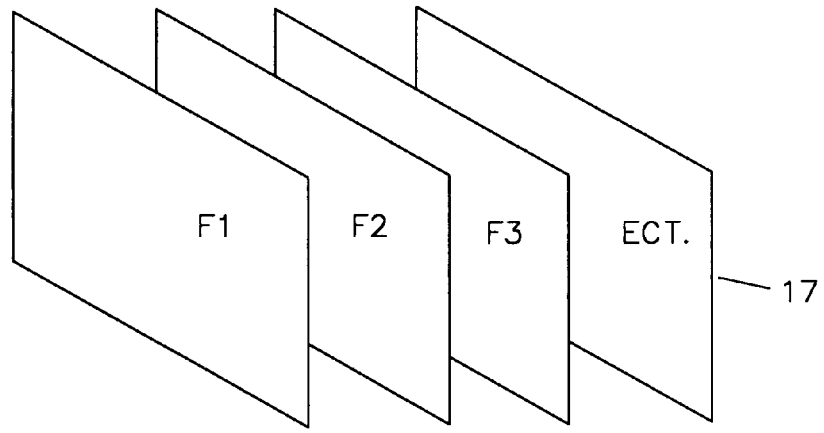

F1  F2  F3  ECT.

17

Highest priority ———————————— lowest priority

Highest risk ———————————— lowest risk

FIG. 6
EMBODIMENT A
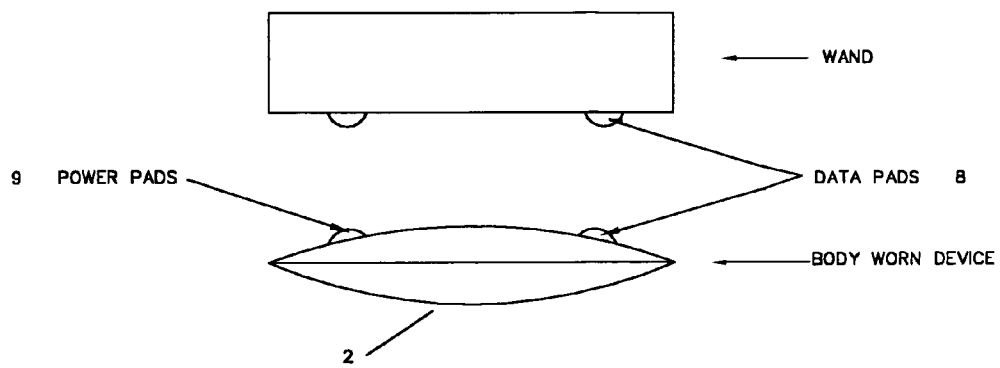
EMBODIMENT B
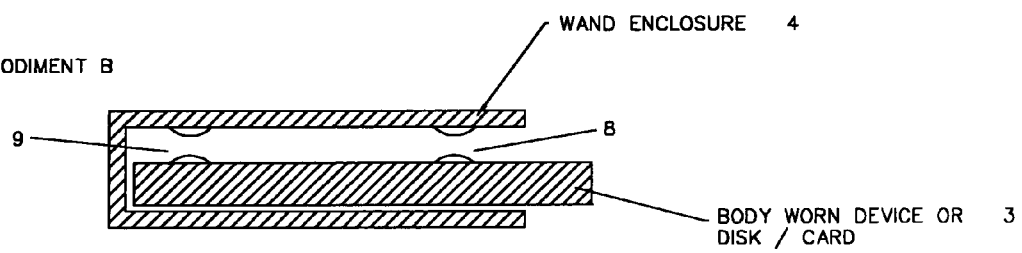
EMBODIMENT C
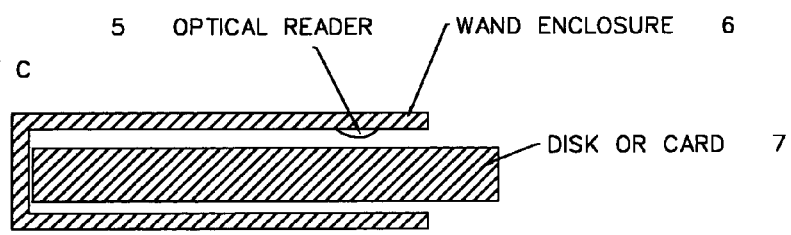

ELECTRONIC SYSTEM FOR RETRIEVING, DISPLAYING, AND TRANSMITTING STORED MEDICAL RECORDS FROM BODILY WORN OR CARRIED STORAGE DEVICES

CROSS REFERENCE OF RELATED APPLICATIONS

The following applications by inventor William Reeves are related to this application:
U.S. Pat. No. 6,467,690
Ser. No. 09/597,107
Ser. No. 09/578,664
It is the intent of this inventor that these related applications, coupled with the application herein, shall comprise an overall system for organizing medical records and other data for access in a medical emergency.

STATEMENT REGARDING FEDERALLY SPONSORED RESEARCH

Not Applicable

COMPACT DISK MATERIALS

Not Applicable

BACKGROUND OF THE INVENTION

Simple bodily worn medical bracelets and medallions have been used for may years by individuals with serious medical conditions to alert emergency medical personnel in the event the wearer is stricken and unconscious that the wearer has a serious pre-existing medical condition which requires special medical treatment. Although these simple bracelets and pendants have been useful they lack the space and storage capacity necessary hold critical lifesaving medical information and any electronics to interface with modern patient monitors and or electronics. Such critical lifesaving information includes: blood type, a description of pre-existing medical conditions, photo ID or other positive identification, ECG scan, Cardiac, Ultrasound scan, present drug usage and interaction cautions, severe drug and other allergic reactions. The invention disclosed herein, and complimentary inventions disclosed by the inventor, teach the design of bodily worn or carried devices which can store large amounts or digital medical records and have those records retrieved in a rapid wireless or contact manner in the event of a medical emergency. The Bodily Worn Device (BWD) can also be embodied into a digital storage card and/or medical computer disk, which is disclosed in another invention by this inventor. Also, other key medical and personal information which can be stored into the bodily worn digital devices include Organ Donor Instructions and Living will instructions which have become very common place and vital to the medical community as well as the individual. Integral to the use of the Bodily worn digital storage devices (BWD) are the inventions disclosed herein which are medical monitors, personal computers, portable display devices and interface electronics used to organize medical records, encrypt the records for security, transmit the records through interface electronics and digitally write the data on computer chips and other suitable storage media located within and part of the BWD. There are a plurality of possible hardware, communications and software configurations for the invention herein. Several of a plurality of embodiments of the invention are disclosed herein, which will most likely be the most convenient and usable commercial versions of the invention.

By disclosing these possible embodiments the inventor is by no means limiting the scope of the invention to said embodiments and the inventor claims the broadest interpretation of said plurality of embodiments. These include: 1. a portable field unit which will include a display screen, microcomputer, interface wand, software, and a means of transmitting data back to a base unit in an emergency 2. an interface module which, in lieu of an entire new patient monitor, can be added to a IU slot in an existing patient monitor and add the capability of accepting data from the Interface Wand and BWD without adding a lot of additional cost to the health care system, 3. a more substantial Base Unit which would be most likely a PC based system and include software for organizing and editing medical data and records, encrypting those records for confidentiality and security, and sending those records directly through the Interface Wand to be digitally written and stored within the BWD in digital storage media such as a computer chip. Although there are many existing and off the shelf software packages currently available there is none which would allow for a concise, highly organized and standard format for displaying of emergency medical records. Since time is of the essence and correct treatment and medical intervention is often a life or death situation it is essential to have the stored medical records in a highly organized, concise standard format so an EMT can go right to the critical information, assess the best medical treatment options and act accordingly. This highlights the need for unique software to organize the emergency medical records and information into concise and edited format for easy use and such software is disclosed herein as part of this invention.

There has been prior art in the medical industry which, although peripherally related to medical records and computer systems, does not teach the art or devices described herein. Doue in U.S. Pat. No. 5,361,202 teaches a computer system and software specifically for the purpose of managing a patients stay in a hospital or clinic. Doue makes no mention of organizing or applying any critical emergency medical information, makes no mention of using or interfacing with Bodily Worn Devices or Medical cards and in general Doue's invention in no way completes with the invention disclosed herein. Since the invention disclosed herein is not used in any way, and makes no claims to manage the time frame for a patients stay in a hospital, these two patents really have nothing more in common than the fact that they use a screen and a microprocessor. Whalen in U.S. Pat. No. 5,327,341 teaches a computer system and software for managing general medical records and files in a hospital and physician office environment. Whalen focuses on the software side of his invention and teaches means of creating headers and organization categories for large amounts of medical information. No where in his invention does Whalen teach organizing Emergency Medical information for emergency medical treatment which is created for the purpose of storage on Bodily Worn and/or Digital Storage cards or disks. Nowhere does Whalen teach any of the Interface Wand, Interface module and data transmission features of the devices disclosed in this invention. The main claims of the Whalen patent deal with managing and updating an individuals medical records in a routine office based setting using key words, hybrid data fields, etc, which this invention is not claiming and for applications this invention has no intention of addressing. Eberhardt in U.S. Pat. No. 5,659,741 teaches a medical history computer system for recording medical histories aimed at organizing very large amounts of medical data for organizations such as the federal government for keeping track of medicare and medicaid and/or for large insurance companies. This differs from the invention disclosed in that the emergency medical data described herein is not stored in a central computer but is organized and stored on Bodily Worn devices. The inventions described herein are patient monitors and interface hardware specifically aimed at retrieving and displaying the stored emergency medical data. Eberhardt fails to teach any of the patient monitors, modules or interface electronic hardware necessary to make the retrieval of emergency medical data a practical device. Although Ebehardt mentions cards or disks to carry medical records he fails to teach any type of practical card or disk and fails to teach how such a card or disk would be interfaced with a practical computer system or its components. An integral part of Ebehardt's inventions, which is not required by the invention disclosed herein, is the ability to sort for medical information and/or data by key word, phrase, etc. This is not necessary for the invention described herein in terms of its software and is outside of the scope of this invention.

SUMMARY OF THE INVENTION

The invention disclosed herein describes several of a plurality of possible embodiments of the invention and its hardware and software configurations. These descriptions are in no way meant to restrict the scope and broadness of the possible embodiments of the invention and it is acknowledged that other embodiments, other than the preferred embodiments described, may be appropriate for use and are incorporated herein. One of a plurality of preferred embodiments may include:

- interface hardware and electronics, embodied in the form of the Interface Wand and module IO card, for electrically powering and retrieving the data from the bodily worn devices in a wireless, non-contact fashion
- software which is compatible with the software and organization platform of the Bodily Worn devices for retrieving, organizing and displaying the stored records in rapid format for emergency situations.
- some form of a screen display which could include an LCD screen, video screen, cathode ray tube, or computer screen for displaying the records in emergency situations.
- a means of periodically updating the records stored on the Bodily worn devices by interfacing the Bodily worn device with the monitors, either using the Interface wand and a direct connection to a monitor or via the wand and an interface box which could be used to modem information into the Bodily Worn device from a remote location using the Internet, Intranet, Wi-Fi, or a plurality of other modem and telecommunications media. Said modem may be used to link the system to the Internet and a website for two way data transmission. The bodily worn device described herein broadly encompasses a digital storage device that can be worn on the body of an individual or carried on a person. Said bodily worn storage device broadly encompasses multiple hardware forms including a bracelet, necklace, pendant, keychain, wrist watch, ring, or other convenient means of wearing or carrying said hardware device, and includes a means of storing digital records within the hardware as described herein
- a means, through unique software encryption and recognition techniques, to interface with unique smart cards and/or unique computer disks which have permanently imbedded software security identification markers. This type of a marker and recognition system allows for only authorized types of disks and card, which have the unique embedded digital markers, to be used and recognized by the system software for security and anti fraud purposes. The alternative, which is an embodiment of this invention, is to have an open architecture software smart software and two way data transmission between the interface hardware and the Bodily Worn devices and cards and disks. This smart software allows for recognition of encrypted security markers to eliminate unauthorized entry to the devices and well as for anti fraud purposes during data transmission.
- electronic cases and enclosures which make the devices herein either rugged and portable for field use and/or military use, enclosures and electronic covers for the module Interface to safely add the module and upgrade to an existing patient monitor, or an enclosure for making the devices desk top and fairly stationary for use in an office environment.

DETAILED DESCRIPTION OF THE INVENTION

Reference FIG. 1

FIG. 1 represents a flow chart of how the integral hardware components of the system would interface. Either the portable field unit, patient monitor module or base unit monitor can send or retrieve data from the Bodily Worn Devices (BWD) via the Interface Wand. In turn, either the Portable Field Unit or the Patient Monitor Module can also send data to and from the Base Unit Monitor via either telephone lines, wireless AM or FM transmission or any other appropriate transmission means. The interface wand is an integral part of the system for sending and retrieving data from the BWD. The Interface Wand has a means of simultaneously sending electrical power to the BWD via wireless inductance means while at the same time sending and retrieving data from the BWD via either optical or capacitance data transmission. The detailed disclosure of the art of the Interface Wand, BWD, Internet and Website features, and other features, are hereby incorporated by reference under the U.S. application Ser. No. 09/578,664 and U.S. Pat. No. 6,467,690. As previously described the portable field unit and the Base unit Monitor both have the electronics to receive and transmit data to and from the Interface Wand, to display medical data on a screen for Emergency Medical treatment, and to send the data wireless or over telephone lines to other stations. The patient monitor module, which is an electronic card which fits into an existing patient monitor, is described in more detail in FIG. 5. Common software allows the devices disclosed herein to communicate, send and retrieve data and encrypt data in secure means for confidentiality and security.

Figure 2:
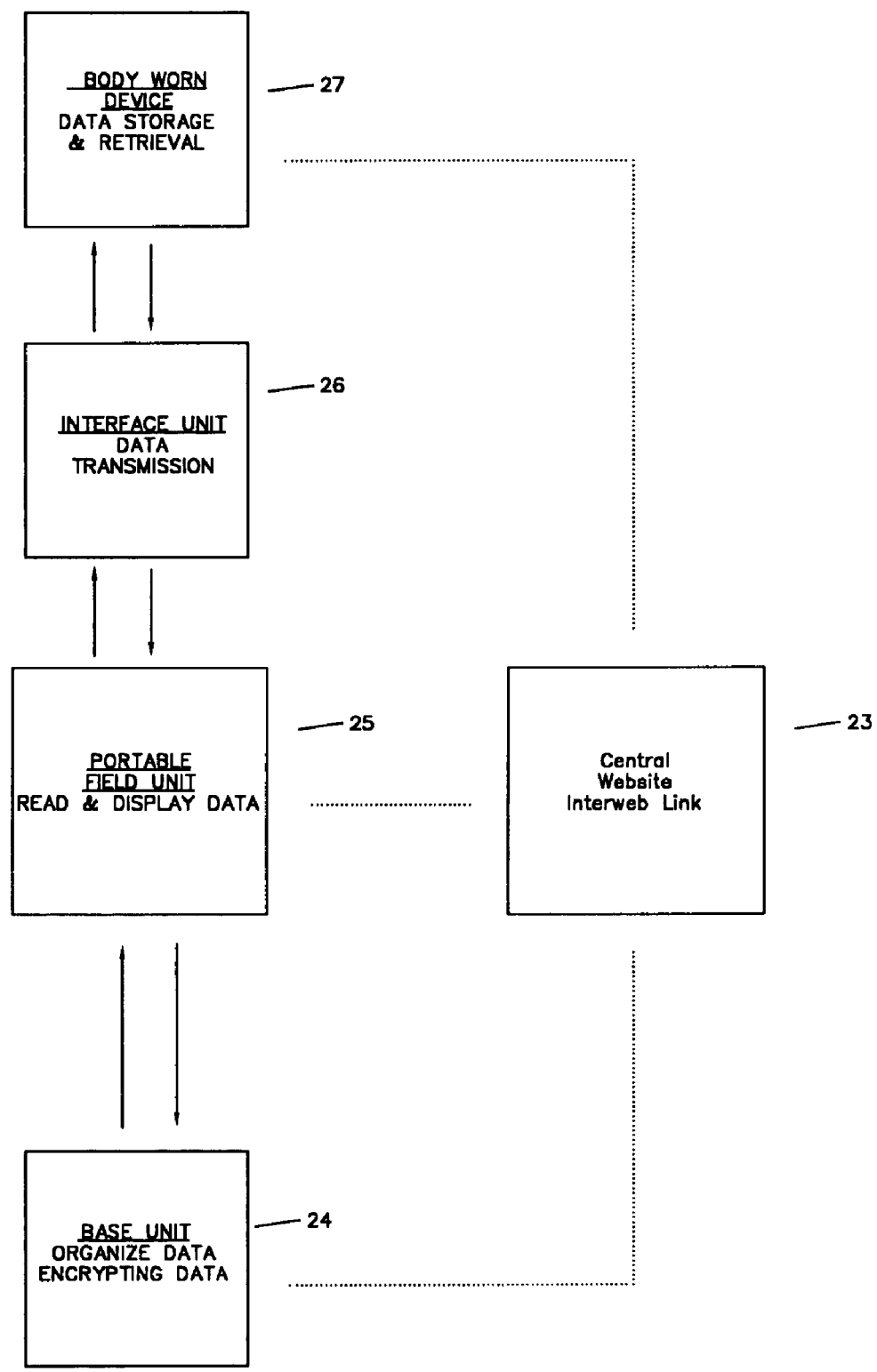

Reference FIG. 2

FIG. 2 shows a schematic of the system operating software and its control and organization of data through the various pieces of hardware in the system. Two-way data transmission is important through each piece of hardware to allow for medical data and records to be both sent and retrieved through the Interface Wand and into and out of the BWD. As shown in FIG. 4 Emergency Medical Records are organized by the software into pages or files with discrete information organized in sections or blocks to create a standard page. The pages are prioritized based on a combination of factors including: clinical relevance in an emergency, chronological order, and a patients pre-existing medical conditions and their relative risks in a medical emergency. This standard page is important because in the event of a medical emergency, where time is critical, a standard page format allows EMT's and technicians to know exactly where to look to get critical life saving information without searching. The software is organized as such so that Emergency Medical records are created for a patient either from the Base Unit, Portable Field Unit or Ambulatory Patient Monitor. The Patient files are encrypted to provide for security during transmission over said modem, telephone, and/or data lines. The software is organized as such so the patient files are transferred through the Interface Unit or Wand into the BWD in file or page format. These patient files are organized through the software into a plurality of standard software formats including ASCII type files so as the be retrievable and readable using standard software packages in conjunction with the unique encryption software described herein. As an alternative and/or enhancement to the encrypting of the medical files security software markers could be written into the medical record files so that only persons with compatible software, which can recognize the security markers, would be allowed to retrieve and open the medical records stored on the system Bodily Worn devices or on system electronic cards or disks described herein.

Figure 3:
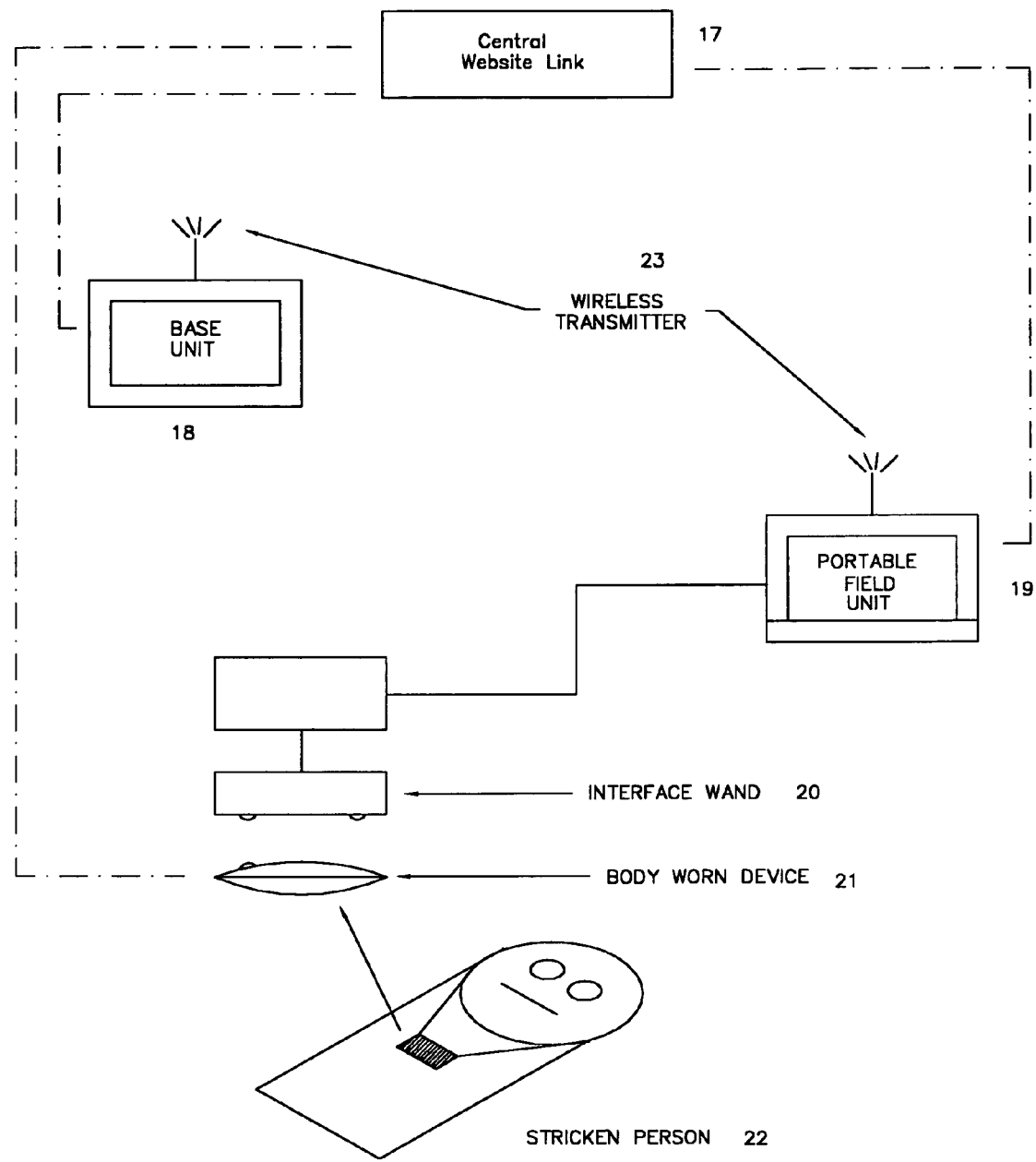

Reference FIG. 3

FIG. 3 is a graphic representation of one of a plurality of possible hardware configurations of the system. FIG. 3 depicts how the main components of the system function in relation to each other including: the Bodily Worn Device, Interface Wand, Portable field unit, Base unit and controlling software. When the wearer of the BWD is stricken with any illness, or is in an accident, or injured in combat an EMT, paramedic, or military corpsman can access the critical medical data using the portable field unit, assess the stricken persons overall condition using the pre-existing medical history and data in the BWD, and rapidly determine the best coarse of medical treatment, which could prove life saving. The portable field unit has the ability to transmit medical data and treatment options to the base unit, in a bi-directional manner, so hospital based medical personnel can communicate directly with the field paramedic via a plurality of media including said modem, wireless communications, or other wireless or hardwired telecommunications media.

An integral part of this invention is the design and electromechanical interface between the BWD, storage cards and storage disks. This is expanded on in FIG. 6 of this invention.

Reference FIG. 4

FIG. 4 shows one of a plurality of possible software configurations for the Emergency Medical Record organization. The medical data can either be in file or page format with discrete blocks or sections of a page devoted to specific information so as to create a standard and easily recognizable format in an emergency situation. Menus or point and click software commands can be set up so as to allow the user to rapidly scroll through pages to find information. As previously described said pages and data fields are organized based on a plurality of factors including: relevance and utility in a medical emergency, chronological order, and a users pre-existing medical condition and the relative risk of said conditions in a medical emergency.

Figure 5:
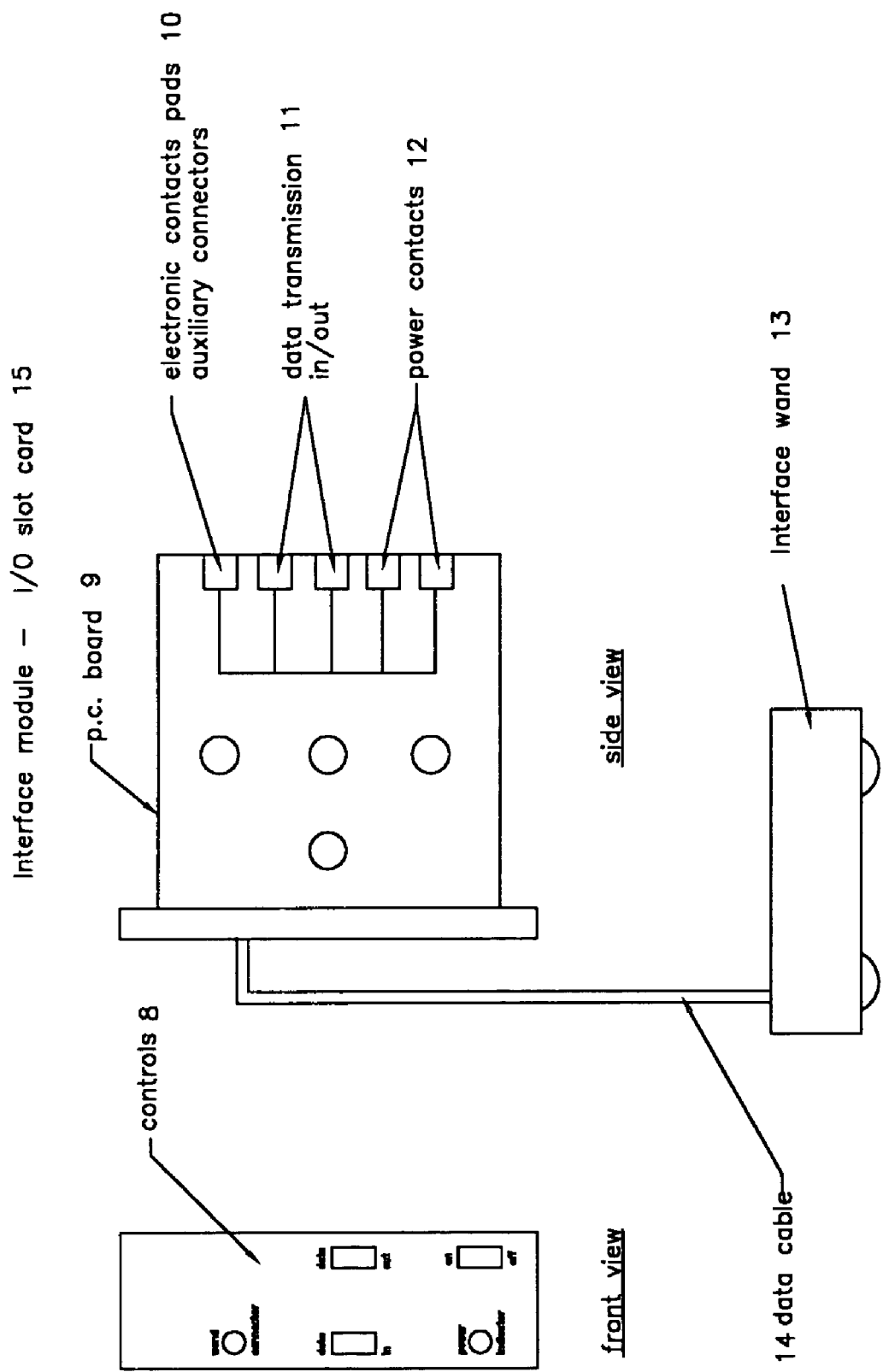

Reference FIG. 5

FIG. 5 shows one of a plurality of possible configurations for the hardware module, which would be used in conjunction with plurality of existing patient monitors including: ambulance monitor, emergency room monitor, and portable monitor. The module depicted in FIG. 5 is one of a plurality of configurations including: a faceplate with controls, switches for on/off power, data transmission indicator lights, power indicator light and any other appropriate controls and indicator lights. An I/O type printed circuit card is mounted to the faceplate and electronic components and circuitry are mounted to the pc board. The electronic circuitry to supply power to the board, as well the circuitry which routes the data signals through the card, are routed to electronic contact pads or fingers as they are known in the industry. The pads are either silver or gold plated and allow the pc board to be plugged into the mating slot in said patient monitor so as to accept electrical power from said patient monitor and allow said medical records and data to be transmitted and received through the pc board and its connecting pads. As previously described the data cable connects the Interface wand to the front panel of the module. The cable allows data to be transmitted from and sent to the Bodily worn devices using either fiber optic, USB, or serial or parallel two-way data transmission.

Reference FIG. 6

As previously mentioned the design and working mechanism of the Interface wand, as it relates to Bodily Worn Device or Card or Disk, is critical. The two devices and their working mechanisms as described herein are unique and novel. This inventor has also written and submitted a separate patent on the Digital Card and Disk and mechanisms to read and transmit data and for means to access system medical records files using the Internet and website features, and other system features. Accordingly U.S. Pat. No. 6,467,690 and application Ser. No. 09/578,664 are incorporated by reference herein. FIG. 6 shows three typical embodiments of this invention and this is not to say that more embodiments do not exist. The Interface wand is designed in Embodiment a) to include a housing, electrical power pads to supply power to the BWD via inductance or other non-contact means, data transmission and retrieval capacitance pads to allow bi-directional flow of digital data in a non-contact manner, a means of aligning the wand and BWD so as to make positive mechanical alignment between the power and data pads.

Embodiment b) shows an alternative design of the Wand whereby a case or slot enclosure in the form of a docking station or port will allow either the BWD, a card or disk to be inserted into the slot. The power pads and data transmission pads are mounted on the interior wall of the enclosure so as to provide protection in the event the wand is dropped or hit. The slot enclosure docking station and BWD, card, disk are designed so the electrical power pads and data pads make proper alignment when the BWD is inserted and hits a mechanical stop in the slot. Data and electrical power can be transmitted in either a contact or non-contact manner.

Embodiment c) shows a wand with a mechanical slot in the form of a port of docking station for insertion of a storage disk or card. In this embodiment an optical read/write pad is utilized, which is one of a plurality of possible embodiments of data exchange. The digital data is stored on an optical film or polymer on the surface of the disk or card, in a similar manner as a compact disk. This data storage embodiment may provide that neither the wand nor disk require any power to retrieve the digital information from the disk. Electrical Power is required to be sent to the optical scanner in the wand so as to power its operation. The bi-directional reading and writing of data to and from the disk or card can be accomplished with a plurality of optical scanner/writer pads mounted to the inside of the wand.

FIG. 7

Figure 7:
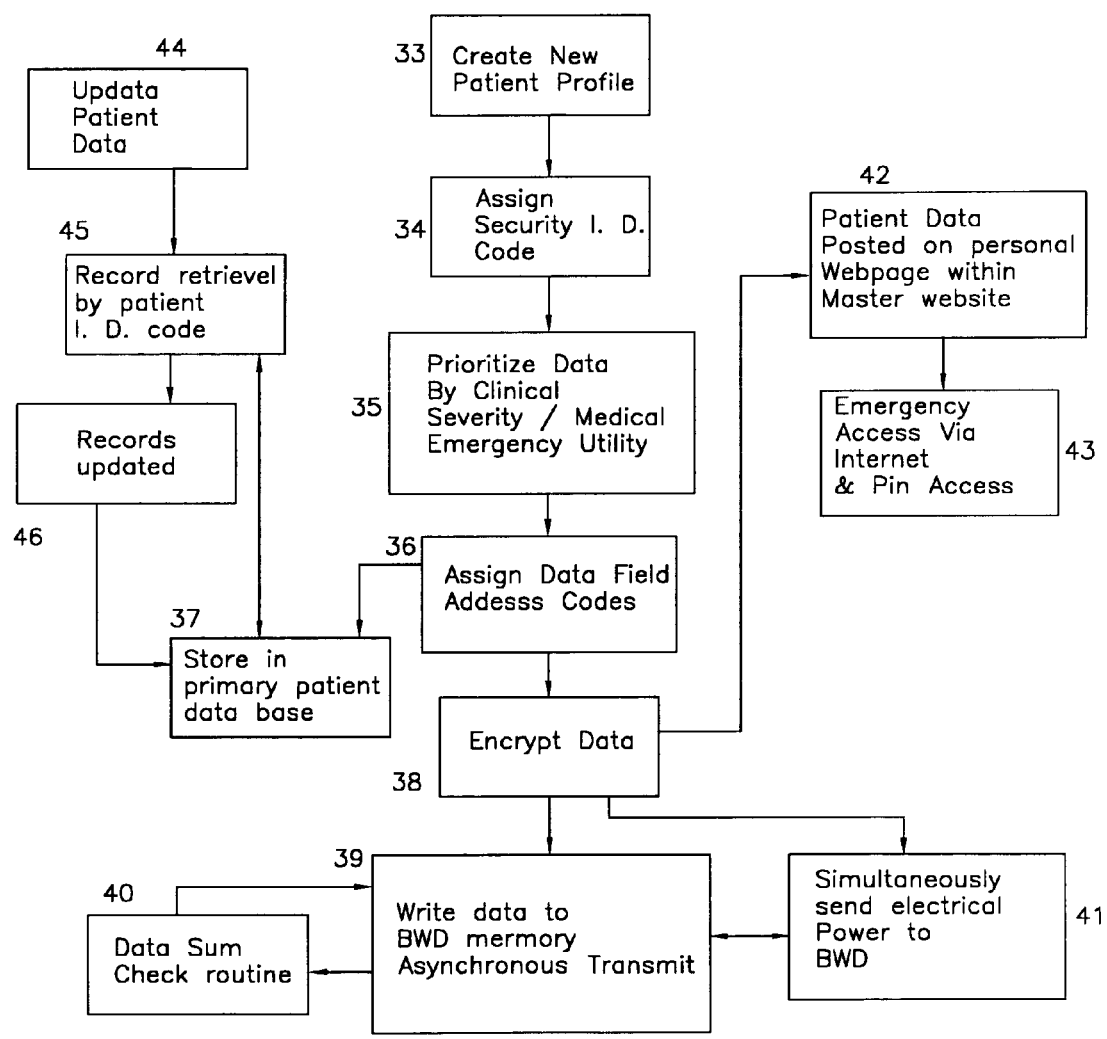
Figure 8:
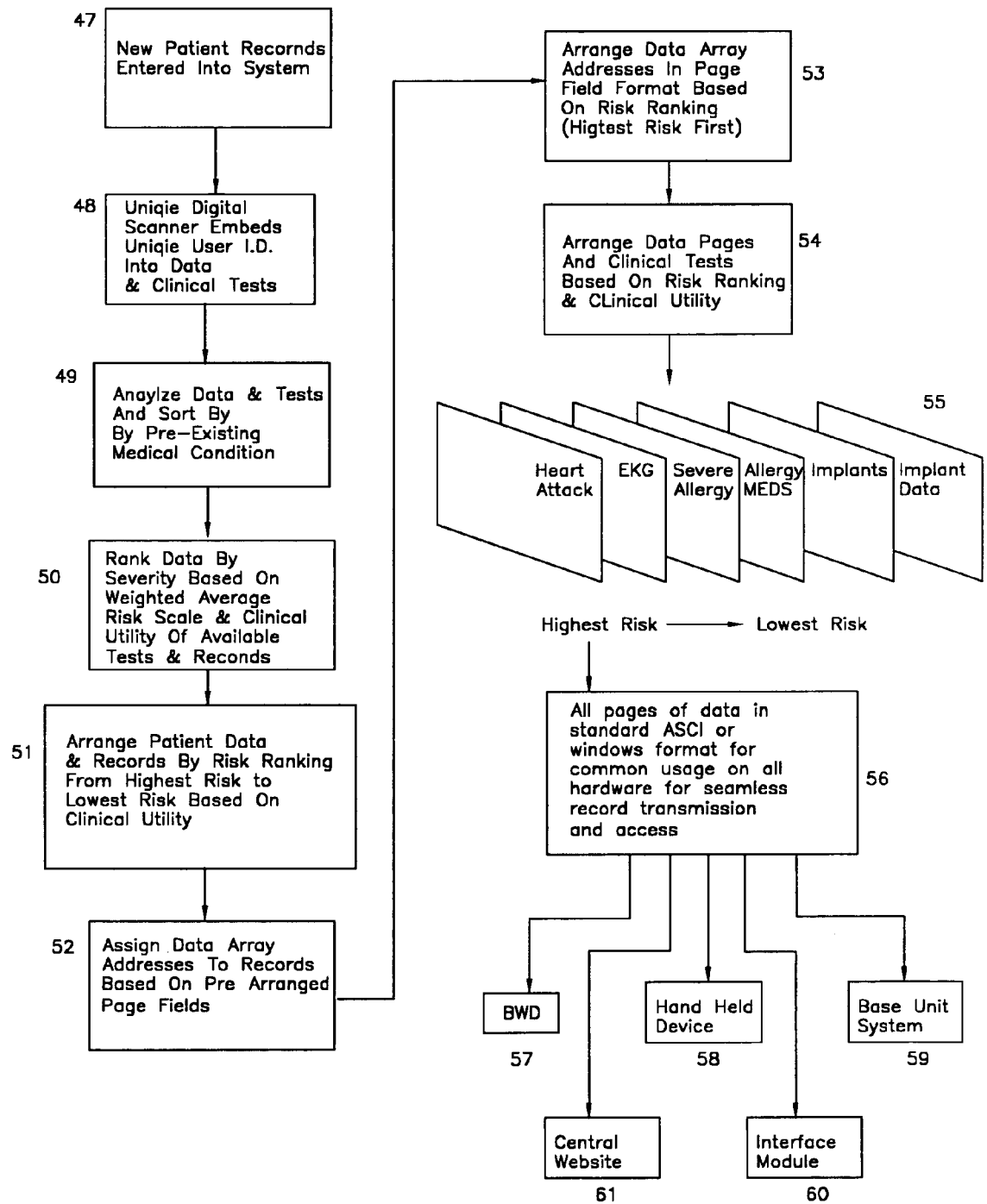

FIG. 7 shows one of numerous preferred embodiments of the software organization, logic and data flow of the system. The software organization, logic, and data flow as described in FIG. 7 are also a method in the broad sense of this patent application. The system is defined as all of the hardware components (bodily worn device and data storage devices, interface wand, hand held unit, patient module, and base unit) and the software which acts as a common language platform for medical records and data to be seamlessly transferred to and from all the hardware devices within the system. The first step of the software organization, logic and data flow is the creation of a new patient profile 33 which is the step whereby either a patient/user or their physician enter the medical data, clinical records, EKG, x-rays, prescriptions and other vital information (which is determined by accessing the patients pre-existing medical conditions, risk factors and the need for accessing said data in an emergency) into the system software via a prearranged data page with data fields. The system software automatically assigns the patient user file with a unique security ID code 34 which is embedded into the patient's data file as a digital watermark. This security ID allows all of the various hardware components of the system to recognize the patient data file as an authentic and valid patient file for security, to avoid tampering or hacking, and to ensure the medical integrity of said data. Step 35 involves the unique process described herein of prioritizing and organizing the medical data by a combination of the weighted averages of the risk factors of the pre-existing medical conditions, the availability of current medical data and records, and the statistical probability of a positive medical outcome when the available medical records are applied to emergency medical diagnosis and treatment. As shown in FIG. 8 the medical data and records are then organized in data fields 36 in page format with the highest risk pre-existing conditions (as determined by the unique risk weighted average) being given highest priority, along with there corresponding medical records and data, on page one, and then lesser medical conditions and there medical data on subsequent pages. The overall purpose of this unique prioritization and records organization is to remove some of the guess work and, at times, faulty cognitive decision making on the part of emergency personnel and physicians, especially at a critical times such as a medical emergency when minutes and seconds routinely count and when the wrong treatment decision often means serious injury or death, partly induced by emergency personnel. Once the medical data has been prioritized and organized each set of data is assigned a unique digital address code which corresponds to a pre-assigned data field on each digital page. This an important step because assignment of a unique address field enables the software to save a great deal of digital memory space when medical data is sent to the bodily worn device-meaning that instead of sending all of the digital data which comprises both the page formats and the medical data, only the medical data need be sent to the bodily worn storage devices and storage devices. The digital addresses assigned to the data enable the system to retrieve the raw medical data from the bodily worn devices, recognize the data's address fields, and route the data to the pre-assigned fields in the pre-arranged data pages. The data can next be automatically encrypted 38 for security and then sent to either directly to the bodily worn device 39 or the data can be encrypted 38 and then sent to the primary patient data base 37 within the system digital archives. The unique process of transmitting data to the bodily worn device 39 in a wireless manner includes several possible modalities including providing a Radio Frequency carrier signal which is produced by the interface wand and digital data is transmitted via the carrier signal to the bodily worn device in asynchronous fashion. Integral to this wireless RF modality is the ability to simultaneously use either inductance means or RF carrier means to wirelessly transmit electrical power to the bodily worn device so as to allow the data to be received, routed and stored in prearranged digital storage space. It should be noted that the bodily worn device 39 contains an RF receiver/transmitter "antenna" which can be in the form of the metal casing protecting the storage device. Additional wireless transmission modalities can include inductance data and power transmission, and short wave high frequency or ultra frequency carrier signals with relatively low power ranges. It should be noted that encrypted data 38 can also be routed to a prearranged system website 42, with prearranged patient data pages, to act as an Internet repository of emergency patient data. This central system website enables medical personnel, in remote locations, to access patient data in a rapid and secure manner via an access pin 43, and provide timely and accurate treatment in a medical emergency (particularly helpful if a patient was traveling to a foreign country). Medical data and medical tests (EKG, x-ray) can be downloaded via the Internet to remote locations for emergency medical treatment. The software system allows for patient data to be updated 44 on a routine basis when a patient's condition or records change, by providing a software update command 44 which in turn generates a patient records retrieval signal 45 which includes the patients unique security ID code. The primary patient database 37 is searched by ID code and patient files are retrieved, records are updated 46, and then records are returned to the primary database 37.

FIG. 8

FIG. 8 provides another diagram which outlines one of numerous preferred embodiments of the overall system software, data flow, organization, and logic. As in FIG. 7 the system is defined as all of the various hardware configurations described herein along with the system software. New patient data and records 47 are entered into the overall system software via either the base unit 59 computer terminal, hand held device 58, patient module 60. New patient records can also be entered and updated from remote locations via a computer and Internet link to the systems central website access portal 61. Patient medical test and data which are in hardcopy paper format may be converted to digital format via a unique scanner configuration 48 (which is further described and disclosed in Ser. No. 09/597,107) which embeds a digital security watermark into each patient test and records to ensure its medical authenticity via the physician signature within the document (which then become a digital physician signature). As previously described (and outlined in FIG. 10) the patient medical records and tests are analyzed by the system software to assess the risk factors of; pre-existing medical conditions, the availability of accurate and up to date medical tests and records, and the prognosis and risk factors of treatment in a medical emergency. The medical records and tests are then ranked and prioritized 50 by a weighted average numerical risk scale from highest risk to lowest risk. Patient records are then organized in order of risk ranking 51 and then the data is assigned data array address codes so as to link the address codes to pre-arranged data fields in records pages 53. The pages and associated clinical tests (EKG, MRI, X-ray, Blood Work, etc.) are then arranged into priority based on risk ranking 54 from highest risk to lowest risk 55. All pages and data are in software languages which are standardized and compatible with exiting patient monitors and hardware systems 56.

FIG. 9

Figure 9:
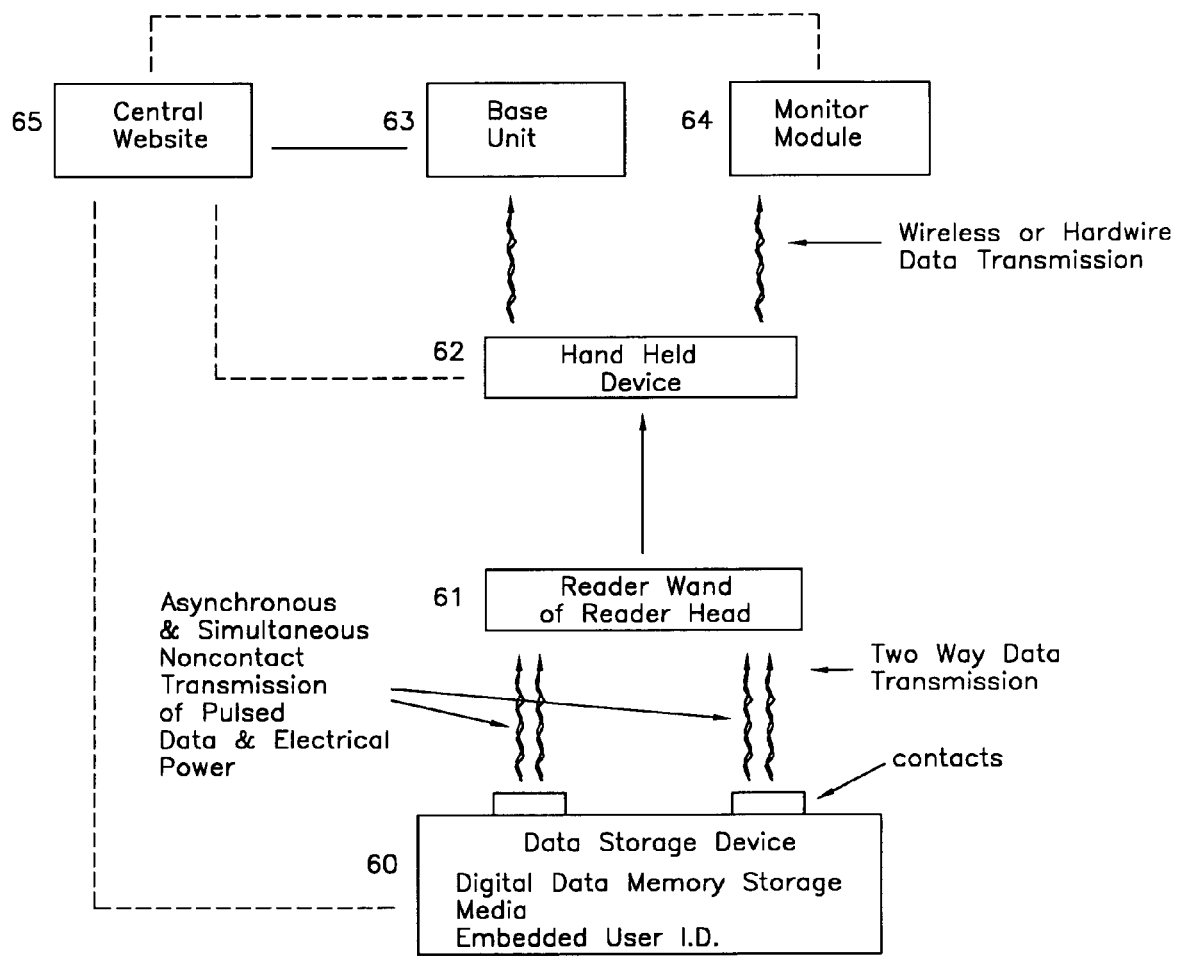

FIG. 9 represents one of a plurality of preferred embodiments of the wireless transmission of data within the overall system. As in FIG. 7 the term system is used herein to denote all of the hardware configurations described in this patent and the unique software used as an integral part of the system. The transfer of data and electrical power to and from the data storage device (BWD) 60 and the reader interface wand 61 takes place via a unique asynchronous radio frequency wireless modality which is described in detail in FIG. 10. Both the interface wand 61 and storage device 60 have a plurality of miniature optical, inductance and radio frequency transmitters and receivers which allow both data and electrical power to be simultaneously send to and from each device. The reader wand 61 is typically hard wired to the hand held device but may also operate in a wireless fashion by similar operating modality. The handheld device 62 can transmit data to the base unit 63, interface module 64 and central website 65 via either wireless or hardwired means. As previously described the central website 65 is also a repository and access portable for the same patient medical records which are stored within the BWD 60. All of the system hardware, including the BWD 60, is linked to the website 65 via either wireless or hardwired means and users and emergency personnel are able to access patient records via a unique serial number which is affixed to the exterior of the BWD 60. Additional redundant system passwords would also be required to ensure that only authorized medical providers have access to patients records and data.

FIG. 10

Figure 10:
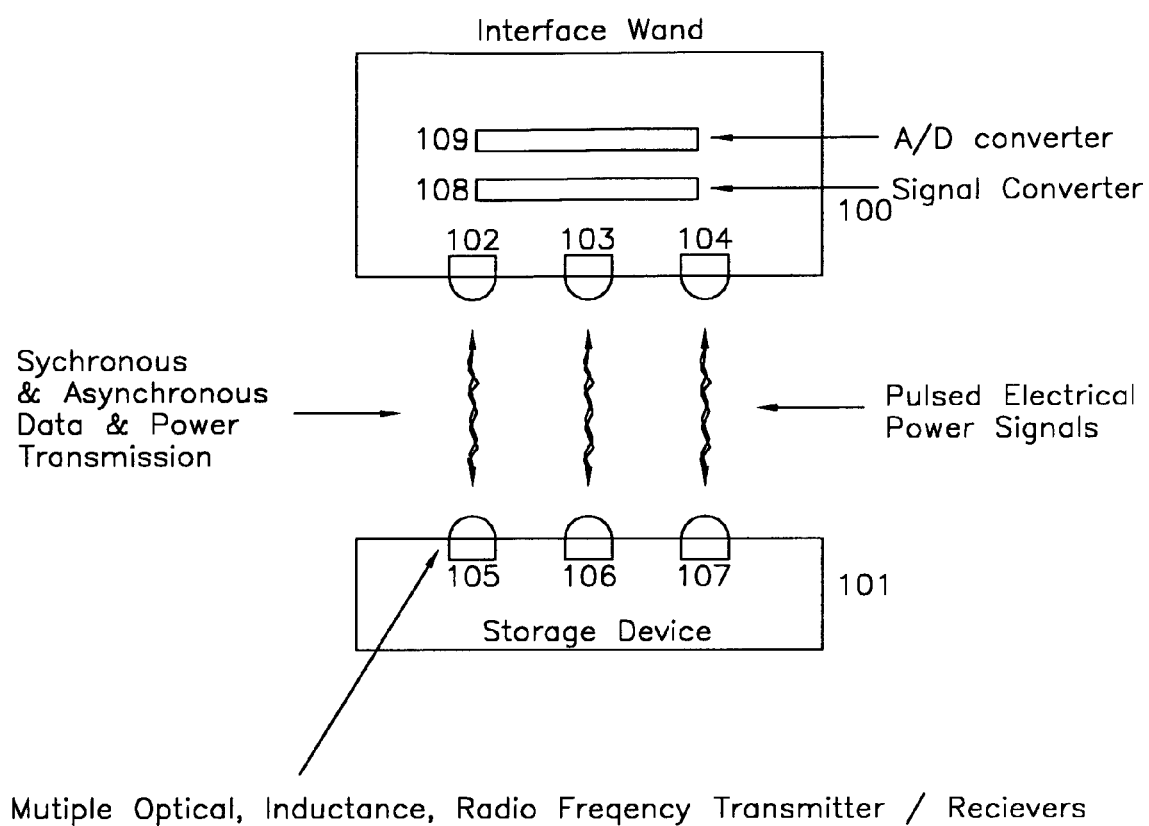

FIG. 10 represents one of a plurality of referred embodiments of the wireless transmission of data and electrical power to and from the bodily worn data storage devices. The same wireless data transmission modality can be used to transmit data from the portable hand held device to the system base unit, patient module and portable hand held device. Interface wand 100 contains a plurality of miniature optical, inductance, radio frequency transmitter/receivers (102,103, 104). The interface wand also include a signal converter 108 which acts to filter, amplify and convert radio frequency and optical signals, routed from the transmitter receivers, into proportional analog or digital signals. Analog to digital converter 109 acts to convert analog data signals to digital format for use within the system software. The wireless data and electrical power transmission to and from the data storage device 101 takes place between the signal transmitters on the interface wand 100 and the receivers 105, 106, 107 within the bodily worn device 101. The preferred modality of wireless transmission of data using either optical or radio frequency signals is an asynchronous pulsed signal modality which transmits discrete packages of digital data to the receivers of the storage device 101. Low power electrical signals are also transmitted via asynchronous pulsed inductance means from the interface wand 100 to the storage device 101. It should be noted that the medical data and records transmitted to the storage device 101 are sent in discrete digital packages so that no A/D converter is required within the storage device 101. The digital data is routed within the storage device 101 to its internal digital storage media (see Reeves U.S. Pat. No. 6,467,690 and Ser. No. 09,578,664 for reference).

FIG. 11

Figure 11:
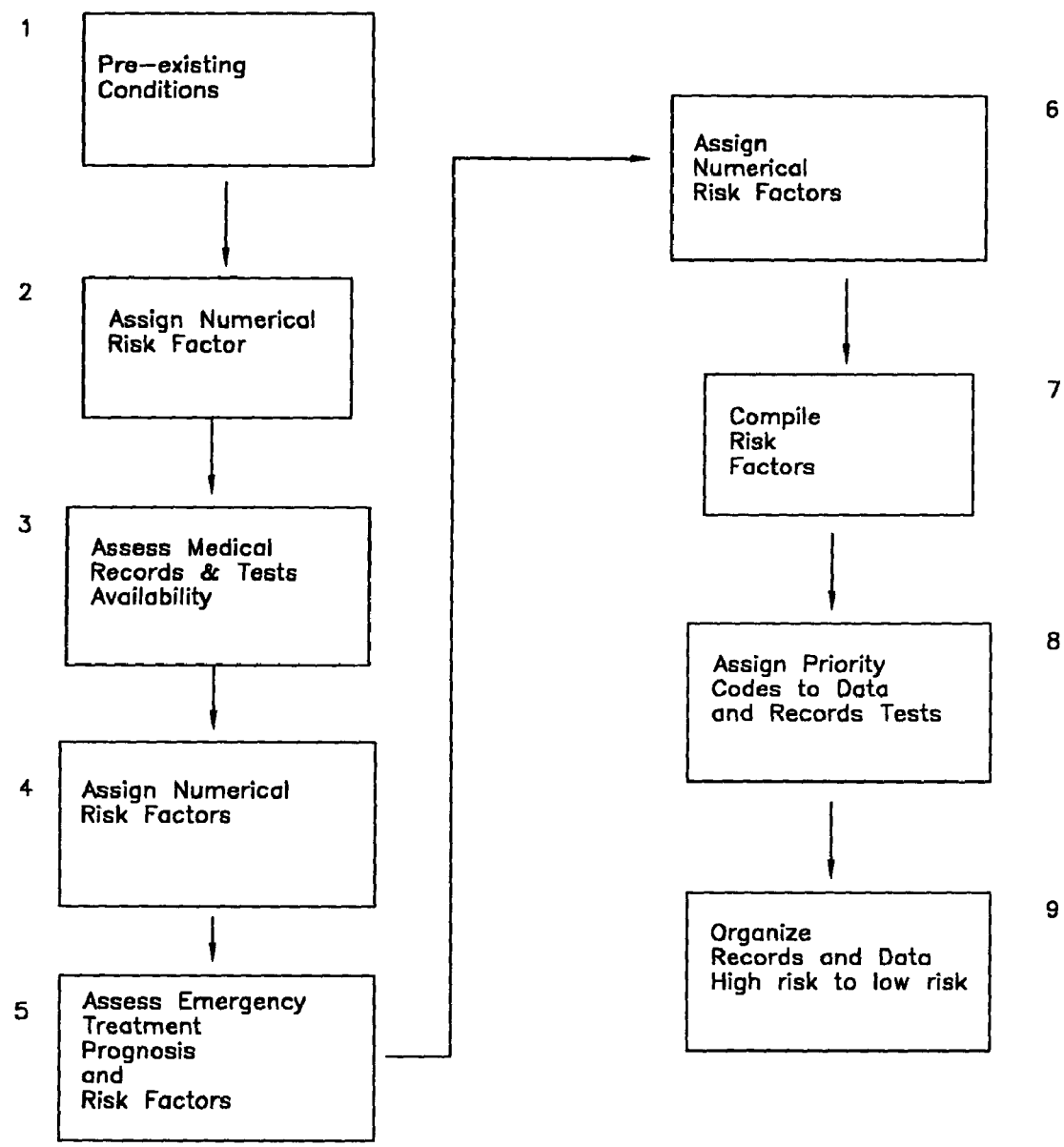

FIG. 11 discloses one of numerous preferred embodiments of the novel prioritization and organization of medical records and data disclosed herein. When a new patient is added to the master system database, or when existing patient records are updated, this prioritization, organization and ranking method is employed by the system software. The system identifies all pre-existing medical conditions 1 and separates them into individual pre-existing condition categories. Next, the system assigns a numerical risk factor 2 to each pre-existing condition 1 based on relative risk to a patient in a medical emergency. Additional numerical risk factors 2 are added for patient age, number of drug prescriptions, body weight, and the potential interaction of the pre-existing conditions. Next the system assesses the quality, accuracy and availability of key medical tests, data and patient information 3 which would reduce patient risk in a medical emergency by providing critical information to physicians for treatment and underlying patient physiology. The system assigns additional risk factors 4 when key data is missing, and assigns reductions 4 to risk factors when key data and tests are present. The system then assesses the statistical probability of prognosis in a medical emergency 5 and assigns additional numerical risk factors 6 (which may add or reduce relative risks). The system then compiles the risk factors 7 and assigns priority codes 8 to all of the patient data, information and medical tests based on the highest risk factor being the highest priority code to the lowest risk factor being the lowest priority code 9.

The system links each pre-existing condition to its corresponding medical test and medical data so as to organize the information for physicians and emergency personnel in a logical and prioritized manner to save the maximum amount of time and provide the highest probability of positive patient outcome in an emergency.

The invention claimed is:

1. A process of storing, retrieving, and organizing digital medical records and other vital personal information from storage devices that can be carried or worn, the process comprising the steps of:
   a) inputting and storing said digital records into said storage devices
   b) providing electrical power to said storage device from an external power source
   c) organizing said digital records in data field and page format within said storage device for ease of use and viewing, accessing and displaying said digital records using portable or stationary computer devices
   d) simultaneously transmitting data and electrical power to and from said storage devices during said docking or porting via non-contact capacitance
   e) transmitting said digital data to and from said storage devices using the Internet, a central website, a modem and other telecommunications modalities
   f) docking or porting said storage device to said computer devices using either non-contact connections
   g) authenticating said storage device by software that recognizes a unique identifier, unique to said bodily worn storage device, and stored within said bodily worn storage device
   h) marking the exterior of said storage device with markings that indicate said device contains said records and vital personal information of said user.

2. The process of claim 1 wherein said step of organizing said digital records further comprises a step of organizing said digital data into condensed medical history pages based on clinical relevance in a medical emergency.

3. The process of claim 2 wherein said step of organizing said digital records into condensed medical history further comprises the steps of placing said data in chronological order and prioritizing said data based on the pre-existing medical conditions of said storage device user.

4. The process of claim 1 wherein said step of inputting said digital records further comprises a step of assigning the digital records to specific data field within a digital page.

5. The process of claim 1 wherein said step of accessing and displaying said digital records further comprises the step of formatting said storage device with system software for seamless use with said computer devices.

6. The process of claim 1 wherein said step of inputting said digital records further comprises the step of encrypting said records for security and confidentiality.

7. The process of claim 1 wherein the step of docking or porting said storage device to said computer device further comprises the step of authenticating said storage device, prior to displaying said records, by comparing said unique identified stored within said storage device to a database of identifiers stored within said computer system.

8. The process of claim 1 wherein the step of authenticating said storage devices further comprises the step of comparing a biometric characteristic of said user that is stored in said storage device to a database of said user biometric characteristics stored in said computer system.

9. The process of claim 1 wherein the step of marking the exterior of said device with unique marking includes the step of marking said device with the users name, telephone number, and other unique personal identification data.

10. The process of claim 1 wherein the step of marking the exterior of said device includes the step of marking the device to indicate that the device contains emergency medical records of said user that can be treat said user in a medical emergency.

11. A system capable of storing, retrieving, and organizing digital medical records and other vital personal information, comprising:
   a) a storage device capable of being carried or worn by a user, wherein the storage device is capable of storing digital medical records and other personal information, wherein the stored digital medical records and other personal information are capable of facilitating emergency medical treatment of the user
   b) hardware component(s) for providing electrical power to said storage device from an external power source
   c) hardware component(s) accessing, reading, writing, erasing, and updating of said digital medical records and personal data of said user stored in said portable device
   d) hardware component(s) for docking or porting said storage device to portable or stationary computer devices to access, view and manage said records and personal information
   e) hardware component(s) for simultaneously transmitting data and electrical power to and from said storage device during said docking or porting via non-contact capacitance
   f) hardware component(s) for recognizing and authenticating said storage device, via a unique digital identifier unique to said storage device and stored in said storage device, when said storage device is ported to said computer devices
   g) hardware component(s) for bi-directional flow of data to and from said storage device from any of said computer devices
   h) hardware component(s) for accessing, displaying, and updating said digital records within said storage device via a modem, Internet, central website, or wireless telecommunications modality
   i) markings on the exterior of said portable device, wherein said markings are capable of indicating that said portable device contains said digital medical records or personal information of said user
   j) hardware component(s) for organize said records and vital personal information in page or template format for ease of viewing and use.

12. The system of claim 11 wherein said storage device and said computer devices are enclosed in a rugged, weatherproof case or enclosure.

13. The system of claim 11 wherein said storage and access of said digital records from said data storage device is via non-volatile memory.

14. The system of claim 11 wherein said portable computers include Palm devices, PDA's, laptops, cell phones, or other portable computer devices.

15. The system of claim 11 wherein said stationary computers include personal computers, computer workstations, existing patient monitors, and patient modules for monitors.

16. The system of claim 11 wherein said digital records and personal information are encrypted for security and to limit access to authorized system users.

17. The system of claim 11 wherein said portable storage device contains software for seamless and rapid communication and transfer of data to and from said computer devices.

18. The system of claim 11 wherein said external power source can include a battery pack, power from a PC, portable computer device, interface wand, docking unit, or other power source modality.

19. The system of claim 11 wherein said simultaneous data and electrical power transfer are accomplished by either non contact capacitance or non contact inductance and at least one carrier frequency.

20. The system of claim 11 wherein said digital records and personal information are accessible from said website via a security password unique to said portable device user.

* * * * *